United States Patent
Markstein et al.

(10) Patent No.: US 7,105,528 B2
(45) Date of Patent: Sep. 12, 2006

(54) BENZO [G] QUINOLINE DERIVATIVES FOR TREATING GLAUCOMA AND MYOPIA

(75) Inventors: Rudolf Markstein, Rheinfelden (DE); Peter Gull, Pfeffingen (CH); Esteban Pombo Villar, Basel (CH)

(73) Assignee: Novartis AG, Basel (CH)

( * ) Notice: Subject to any disclaimer, the term of this patent is extended or adjusted under 35 U.S.C. 154(b) by 224 days.

(21) Appl. No.: 10/483,310

(22) PCT Filed: Jul. 8, 2002

(86) PCT No.: PCT/EP02/07594

§ 371 (c)(1),
(2), (4) Date: Jan. 8, 2004

(87) PCT Pub. No.: WO03/006458

PCT Pub. Date: Jan. 23, 2003

(65) Prior Publication Data

US 2004/0171628 A1 Sep. 2, 2004

(30) Foreign Application Priority Data

Jul. 9, 2001 (EP) ........................... 01116553

(51) Int. Cl.
*A61K 31/505* (2006.01)
*A61P 27/02* (2006.01)
*C07D 401/12* (2006.01)

(52) U.S. Cl. ................. 514/269; 544/316; 544/331
(58) Field of Classification Search ............... 514/269; 544/316, 331
See application file for complete search history.

(56) References Cited

U.S. PATENT DOCUMENTS 5,262,422 A 11/1993 Gull et al.

6,057,334 A * 5/2000 Gull et al. .................. 514/290

FOREIGN PATENT DOCUMENTS

| EP | 0 512 952 | 11/1992 |
| EP | 0 659 430 | 6/1995 |
| WO | WO 97 03054 | 1/1997 |
| WO | WO 98 01444 | 1/1998 |

* cited by examiner

Primary Examiner—Kamal A. Saeed
(74) Attorney, Agent, or Firm—Susan Hess

(57) ABSTRACT

The invention provides a compound of formula I

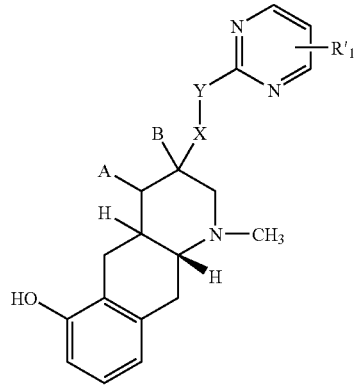

wherein A, B, X, Y and $R_1$ are as defined in the description, and a process for preparing them. The compounds of formula I are useful as pharmaceuticals.

5 Claims, No Drawings

BENZO [G] QUINOLINE DERIVATIVES FOR TREATING GLAUCOMA AND MYOPIA

The present invention relates to novel benzo [g] quinoline derivatives, their preparation, their use as pharmaceuticals and pharmaceutical compositions containing them.

More particularly the present invention provides a compound of formula I

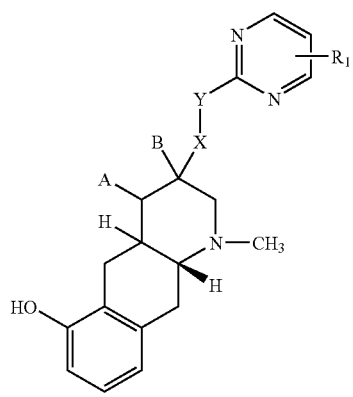

wherein
A and B are each H or form together an additional bond,
X is $CH_2$ or CO,
Y is O, S, $NR_2$ [$R_2$ being H or ($C_{1-4}$)alkyl], $CH_2$ or O—$CH_2$, and
$R_1$ is H or ($C_{1-4}$)alkyl
in free base or acid addition salt form.

The above-defined alkyl groups preferably represent methyl.

When A and B are each H, the X—Y-pyrimidine substituent preferably presents the configuration 3R.

X is preferably $CH_2$.

Y is preferably O or S, even more preferably S.

$R_1$ is preferably methyl, more preferably methyl in position 4 of the addressed pyrimidine.

In a preferred embodiment A and B each represents H, X is $CH_2$, Y represents S and $R_1$ is methyl.

In a further aspect the invention provides a process for the production of the compounds of formula I and their acid addition salts, whereby in a compound of formula II

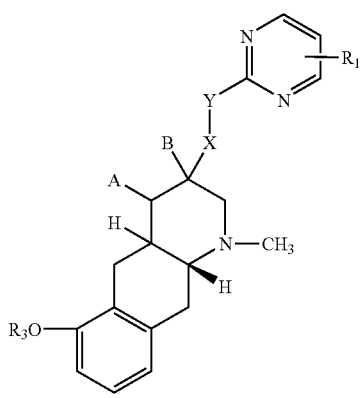

wherein A, B, X, Y and $R_1$ are as defined above and $R_3$ is ($C_{1-4}$)alkyl, the alkoxy group is converted into a hydroxy group, and the compounds of formula I thus obtained are recovered in free base or acid addition salt form.

The reaction can be effected according to known methods, e.g. using hydrobromide acid or boron tribromide. In formula II, $R_3$ is preferably methyl.

Working up the reaction mixtures obtained according to the above process and purification of the compounds thus obtained may be carried out in accordance to known procedures.

Acid addition salts may be produced from the free bases in known manner, and vice versa. Suitable acid addition salts for use in accordance with the present invention include for example the hydrochloride.

The starting compounds of formula II wherein A and B are each H may be produced from the corresponding compounds of formula $III_a$

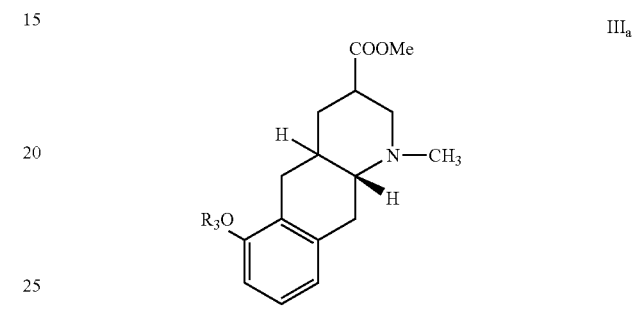

wherein $R_3$ is as defined above, for example as described in Example 1.

The compounds of formula $III_a$ are known or may be produced in analogous manner to known procedures.

The starting compounds of formula II wherein A and B together form an additional bond may be produced from the corresponding compounds of formula $III_b$

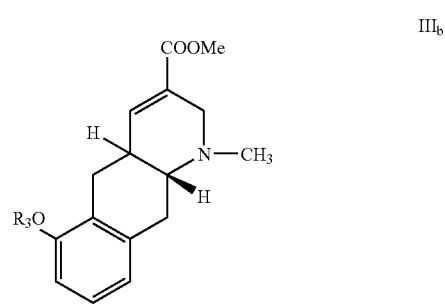

wherein $R_3$ is as defined above.

The compounds of formula $III_b$ are known or may be produced in analogous manner to known procedures.

The compounds of formula I and their physiologically acceptable acid addition salts, referred to hereinafter as agents of the invention, exhibit valuable pharmacological properties in animal tests and are therefore useful as pharmaceuticals.

In particular, the agents according to the invention effect a decrease on the intraocular pressure in rabbits, at concentrations of e.g. 10 to 100 µM. Male rabbits of ca. 2.5 kg are fixed in cages leaving their heads free. The solutions with the compound to be tested are applied to the right eye and the placebo solutions to the left eye (2 drops each, i.e. ca. 40 µl). The eyes are firstly anaesthetized with a solution containing Novesine (0.4%) and Fluorescein (0.05%) and the ocular pressure is determined at various intervals after administration (10, 20, 30, 60, 90, 120, 180 and 240 minutes), whereby an applanation tonometer according to Goldberg is used.

The agents of the present invention, in particular the preferred agents, exhibit a surprising strong efficacy in lowering the intraocular pressure (IOP) and an excellent duration of action. Moreover, they exhibit an excellent tolerability.

The agents according to the invention are therefore in particular useful in the treatment of glaucoma and myopia. A more preferred use is glaucoma treatment, lowering of IOP.

For the above mentioned indication, the appropriate dosage will of course vary depending upon, for example, the compound employed, the host, the mode of administration and the severity of the condition being treated. However, in general, satisfactory results in animals are indicated to be obtained at a daily dosage of from about 0.1 to about 10 mg/kg animal body weight. In larger mammals, for example humans, an indicated daily dosage is in the range from about 5 to about 200 mg, preferably about 10 to about 100 mg of the compound conveniently administered in divided doses up to 4 times a day or in sustained release form.

The agents of the invention may be administered in free form or in pharmaceutically acceptable salt form. Such salts may be prepared in conventional manner and exhibit the same order of activity as the free compounds.

Accordingly the present invention provides an agent of the invention for use as a pharmaceutical, e.g. in the treatment of glaucoma and myopia.

The present invention furthermore provides a pharmaceutical composition comprising an agent of the invention in association with at least one pharmaceutically acceptable diluent or carrier. Such compositions may be formulated in conventional manner. Unit dosage forms contain, for example, from about 0.25 to about 50 mg of an agent according to the invention.

Agents according to the invention may be administered by any conventional route, for example parenterally e.g. in form of injectable solutions or suspensions, or enterally, preferably orally, e.g. in the form of tablets or capsules.

More preferably, they are applied topically to the eye in about 0.0001 to 2%, preferably in about 0.001 to 0.5%, and more preferably in about 0.01 to 0.1% ophthalmological solutions.

The ophthalmic vehicle is such that the compound is maintained in contact with the ocular surface for a sufficient time period to allow the compound to penetrate the corneal and internal regions of the eye.

The pharmaceutically acceptable ophthalmic vehicle may be e.g. an ointment, vegetable oil, or an encapsulating material.

In accordance with the foregoing, the present invention also provides an agent of the invention for use as a pharmaceutical in the treatment of glaucoma and myopia.

Moreover the present invention provides the use of an agent of the invention, for the manufacture of a medicament for the treatment of glaucoma and myopia.

In still a further aspect the present invention provides a method for the treatment of glaucoma and myopia in a subject in need of such treatment, which comprises administering to such subject a therapeutically effective amount of an agent of the invention.

The present invention relates also to any compound disclosed in the working examples. It further relates to any independent and/or dependant claims disclosed infra.

The following examples illustrate the invention. The temperatures are given in degrees Celsius and are uncorrected.

EXAMPLE 1

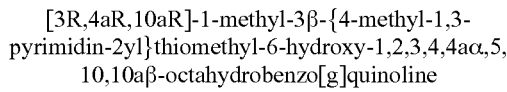

a) [3R,4aR,10aR]-1-methyl-3β-hydroxymethyl-6-methoxy-1,2,3,4,4aα,5,10, 10aβ-octahydrobenzo[g]quinoline To a solution of 5.78 g (20 mM) [3R,4aR,10aR]-1-methyl-3β-methoxycarbonyl-6-methoxy-1,2,3,4,4aα,5,10, 10aβ-octahydrobenzo[g]quinoline in 100 ml toluene, a solution of 12 ml SDBA (70% in toluene, 42 mM) is added in drops under argon at room temperature within one hour. Then 10 ml NaOH (30%) are added in drops to the ice cooled reaction mixture. The precipitated crystals are filtered off, washed with water and toluene and dried. The resulting title compound has a m.p. of 148°; $[\alpha]^{20}_D = -120°$ (c=0.425 in ethanol).

b) [3R,4aR,10aR]-1-methyl-3β-mesyloxymethyl-6-methoxy-1,2,3,4,4aα,5,10,10aβ-octahydrobenzo[g]quinoline 12 ml (153 mM) methanesulfochloride are added in drops to a solution of 20 g (76.5 mM) of the compound obtained under a) in 150 ml pyridine at room temperature. The temperature is kept below 45° by ice cooling. After stirring for 2 hours at room temperature, the solution is adjusted to pH 7–8 with saturated $KHCO_3$ solution at 0° and extracted with ethylacetate. After drying over $Na_2SO_4$, filtering and concentrating by evaporation, the title compound is obtained as beige crystals and directly used for the next step.

c) [3R,4aR,10aR]-1-methyl-3β-{4-methyl-1,3-pyrimidin-2yl}thiomethyl-6-methoxy-1,2,3,4,4aα,5,10,10aβ-octahydrobenzo[g]quinoline A solution of 6 g (17.7 mM) of the compound obtained under b) and 3.4 g (27 mM) 2-mercapto-4-methyl-1,3-pyrimidin in 60 ml dimethylformamide is mixed with 6 ml 2N NaOH and stirred at 65° for 18 hours. The so obtained suspension is concentrated by evaporation. The crude product crystallises. The suspension is cooled to 5–10°, washed with ethylacetate and dried. Chromatography on silicagel with ethylacetate containing 10% ethanol and 0.01% $NH_3$ yields the title compound as beige crystals.

d) [3R,4aR,10aR]-1-methyl-3β-{4-methyl-1,3-pyrimidin-2yl}thiomethyl-6-hydroxy-1,2,3,4,4aα,5,10,10aβ-octahydrobenzo[g]quinoline To a solution of 4.06 g (11 mM) of the product obtained under c) in 250 ml methylenechloride, 40 ml of boron tribromide (1 M in methylenechloride) are slowly added in drops at a temperature of −40°. The suspension is stirred for 2 hours at room temperature, neutralized with $NH_3$ and extracted with a mixture of 150 ml methylenechloride and 100 ml isopropanol. After drying over $Na_2SO_4$, filtering and concentration by evaporation, the title compound crystallises. The corresponding hydrochloride crystallises from methanol/ethanol 1:1 during evaporation. M.p. 254°; $[\alpha]^{20}_D = -90°$ (c=0.540 in ethanol/water 1:1). $C_{20}H_{25}N_3OS$ (HCl), MW=391.97.

What is claimed is:

1. A compound of formula I

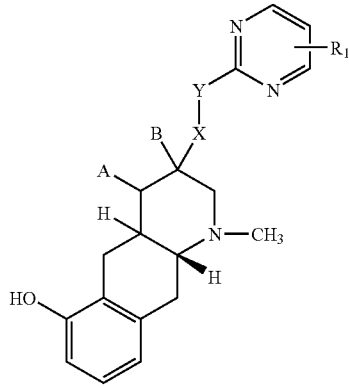

wherein

A and B are each H or form together an additional bond,

X is $CH_2$ or CO,

Y is O, S, $NR_2$ [$R_2$ being H or ($C_{1-4}$)alkyl], $CH_2$ or O—$CH_2$, and $R_1$ is H or ($C_{1-4}$)alkyl in free base or acid addition salt form.

2. The compound of formula I, wherein A and B are each H, X is $CH_2$, Y is S and $R_1$ is methyl.

3. A process for the preparation of a compound of formula I as defined in claim 1, or a salt thereof, which includes the step of converting, in a compound of formula II

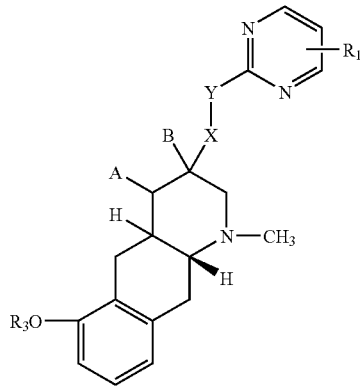

wherein

A and B are each H or form together an additional bond,

X is $CH_2$ or CO,

Y is O, S, $NR_2$ [$R_2$ being H or ($C_{1-4}$)alkyl], $CH_2$ or O—$CH_2$, and $R_1$ is H or ($C_{1-4}$)alkyl, and $R_3$ is ($C_{1-4}$)alkyl, the alkoxy group into a hydroxyl group to form the compound of formula I, and recovering the compound of formula I in free base or acid addition salt form.

4. A pharmaceutical composition comprising a compound of claim 1 in free base or pharmaceutically acceptable acid addition salt form, in association with a pharmaceutical carrier or diluent.

5. A method for the treatment of glaucoma and myopia in a subject in need of the treatment, which comprises administering to such subject a therapeutically effective amount of a compound of claim 1 in free base or pharmaceutically acceptable acid addition salt form.

* * * * *